| United States Patent [19] | [11] Patent Number: 4,754,079 |
| Bison et al. | [45] Date of Patent: Jun. 28, 1988 |

[54] PROCESS FOR PRODUCING THE SODIUM SALT OF 2-NITRO-1,3-PROPANEDIOL

[75] Inventors: Gunter Bison; Hans Leuck, both of Troisdorf; Klaus Thewalt, Witten; Hans-Jorg Westerman, Troisdorf, all of Fed. Rep. of Germany

[73] Assignee: Dynamit Nobel AG, Troisdorf, Fed. Rep. of Germany

[21] Appl. No.: 29,093

[22] Filed: Mar. 23, 1987

[30] Foreign Application Priority Data

Sep. 21, 1985 [DE] Fed. Rep. of Germany ....... 3533801

[51] Int. Cl.[4] .............................................. C07C 79/18
[52] U.S. Cl. .................................................... 568/712
[58] Field of Search .......................................... 568/712

[56] References Cited

U.S. PATENT DOCUMENTS

| 3,534,112 | 10/1970 | Tindall | 568/712 |
| 3,560,575 | 2/1971 | Tindall | 568/712 |
| 3,651,144 | 3/1972 | Tindall | 568/712 |
| 3,723,561 | 1/1973 | Wessendorf | 568/712 |
| 4,215,228 | 7/1980 | Baum et al. | 568/712 |
| 4,581,178 | 4/1986 | Milstein | 558/409 |

Primary Examiner—Werren B. Lone
Attorney, Agent, or Firm—Antonelli, Terry & Wands

[57] ABSTRACT

A safe production of sodium nitro-1,3-propanediol from a reaction solution of nitromethane and paraformaldehyde in methanol by addition of sodium methylate is achieved by evaporative cooling of the methanol; it being possible to maintain reaction temperatures of 35° C. to 50° C.

9 Claims, No Drawings

PROCESS FOR PRODUCING THE SODIUM SALT OF 2-NITRO-1,3-PROPANEDIOL

This invention relates to the production of the sodium salt of 2-nitro-1,3-propanediol, especially of the adduct of methanol (called aci-salt) from methanolic reaction solutions of nitromethane, paraformaldehyde and alkali, by further reaction with sodium methylate.

Such production is conventional, but the known process must be carried out at temperatures of between 0° and 25° C. with careful metering of the starting materials. In this process, the reaction product forms a metastable solution from which the aci-salt is suddenly precipitated after attaining a 5- to 10-fold supersaturation. In addition to the heat of reaction, the considerable heat of crystallization is released within a short time period and results in a strong rise in temperature.

Since the aci-salt can decompose above 50° C. into substances constituting explosion hazards, decomposition is suppressed by vigorous cooling and interrupting the feed of sodium methylate.

However, the low reaction temperatures of at most 25° C. require a reaction period of several hours. For this reason, efforts have been made to increase the yields and, respectively, to shorten the residence time by providing excess amounts of 10-20% of paraformaldehyde or sodium methylate, or both compounds. These excess amounts over the stoichiometric quantity, however, are lost and additionally require high expenditure for purification without a substantial drop in the reaction periods, so that the proportion of personnel costs in the manufacturing expenses becomes high, and large installations with high investment costs become necessary.

Therefore, the invention is based on the objects of reducing the reaction period of the process and, if at all possible, with the yield remaining the same, of reducing the amount of consumed sodium methylate and paraformaldehyde.

It has been found surprisingly that the reaction temperature can be raised without the formation of compounds constituting explosion hazards. In contrast to the heretofore encountered reaction period of several hours, the reaction can then take place surprisingly within a few minutes, e.g., from about 10-25 minutes. The process according to the invention can then use substantially smaller apparatuses.

Adequate safety, though, is only attainable by the measures according to this invention, avoiding with great safety a sudden increase in the temperature.

Therefore, the invention relates to a process for producing the sodium salt of 2-nitro-1,3-propanediol by reacting methanolic reaction solutions of nitromethane with paraformaldehyde containing alkali hydroxide by means of further reaction with sodium methylate in a methanolic solution, characterized in that the reaction solution and/or the residual solution from the production of the sodium salt of 2-nitro-1,3-propanediol is conveyed along one route to a reactor, and sodium methylate in a methanolic solution is conveyed along another route to the reactor, and that the reaction temperatures are maintained at between 35° and at most 50° C. by evaporative cooling of vaporizing methanol by regulating the pressure in the reaction vessel, which pressure is maintained below normal pressure.

It has been found, in particular, that evaporating methanol and thus evaporative cooling alone is sufficient to safely avoid temperatures at which decomposition occurs and, on the other hand, to make possible temperatures at which the above-mentioned reaction proceeds very rapidly.

In order to get the respective reaction temperatures, regulation of the reduced pressure in the reaction vessel is utilized, by means of a device maintaining the pressure constant at such pressure values at which, at the respective reaction temperatures, evaporation of the methanol takes place in the vessel. In case of maintaining a constant pressure, the reaction can also be controlled by way of the temperature.

It has been found that cooling by vaporization of methanol in the reaction vessel is so effective that sudden rises in temperature are avoided, and reaction temperatures are possible up to close to the decomposition temperature of the aci-salt, i.e., temperatures within the range from 35° to 50° C. Furthermore, at these reaction temperatures, the reaction time drops to a few minutes. Thereby, residence time in the vessel is determined practically merely by handling, and no longer by the duration of the reaction.

A practically complete yield of 97.5% or more can now be achieved with excess amounts of paraformaldehyde of only 3-10 mol-%, preferably 4-6 mol-%, above the stoichiometrically calculated quantity of 2 moles of paraformaldehyde per mole of nitromethane in the reaction solution. Also the excess amount of sodium methylate need be merely 3-10, preferably 4-6 mol-% above the stoichiometric quantity.

The product of the process is separated from the reaction solution with a superior purity of 99% or more, so that purification is unnecessary. Few by-products are contained in the remaining mother liquor so that the liquor can be reused in the reaction after enrichment with additional reactive compounds.

The reactor is equipped with an agitator and has a condenser attached for receiving the evaporated methanol, as well as an installation to keep the vacuum continuous or constant.

Preferably, sodium methylate is introduced under pressure in a methanolic solution, in a concentration of 25-35% by weight, separately from the remaining reactants, by means of a pump. In case of a discontinuous performance of the reactions, the suspension, after the aci-salt has been precipitated, is emptied under cooling into the receiver of the filter. Several batches per hour can be accomplished. The reaction can be conducted with considerable advantage in the same vessel, after formation of the suspension of the aci-salt, by feeding further starting compounds and with continuous discharging of the product, without a drop in the degree of conversion. At the temperatures of the process according to this invention, the reaction velocity is so high that nitromethane does not pass in an appreciable amount into the condenser with the evaporating methanol.

The reaction is regulated by way of a predetermined pressure or a predetermined temperature; desired temperature changes can be effected by desired value adjustment of the system pressure. Coupled pairs of temperature and pressure for methanol are known from tables.

Consequently, the pressure during the reaction within the reactor ranges between 50 and 800 mb in dependence on the respective reaction temperature.

According to the invention, the heretofore missing high operating safety is thus attained, in particular, by the measure of evaporative cooling, and additionally corresponding feeding, a substantially shorter reaction time is achieved with increased yield and substantially reduced process costs.

In the following examples, "%" means in all cases "% by weight."

EXAMPLE 1

A reaction vessel (reactor I) equipped with agitator and condenser for evaporating methanol, as well as device for keeping the pressure constant, was filled with methanol and a vacuum was set of 395 mb. The following streams were fed in metered amounts from the receiving tanks over three hours.

(a)
22.893 kg of so-called clear solution, consisting of the condensation products of
  2,832 g of nitromethane (95–96%)
  2,982 g of paraformaldehyde (98.7%) (about 5.5% excess)
  14 g of KOH (30% in $H_2O$)
  17,065 g of methanol (b)
8.77 kg of sodium methylate (30% in methanol).
  This corresponds to an excess of about 5% of sodium methylate.

The reaction vessel was not equipped with cooling units. After a short time (about 10 minutes), the temperature rose to 43.5° C. and was maintained constant at this value. The resulting aci-salt suspension passed via an overflow and a barometric plunger conduit into a cooled vessel (reactor II) held under normal pressure and from there to a suction filter where, at room temperature, the salt was separated from the mother liquor. The average residence times in this process were about 3 minutes for reactor I, about 1 minute for the plunger conduit, and about 10 minutes for reactor II. The filter cake was dried under vacuum.

The dry product weighed 8.917 kg, corresponding to a yield of 97.5%. Purity above 99.6%.

EXAMPLE 2

A reactor of 2-liter capacity, equipped as in Example 1, was charged with 300 g of so-called clear solution (composition as in Example 1), and a vacuum was applied of about 400 mb. Within two minutes, 115 g of sodium methylate (same excess as in Example 1) was uniformly fed into the reactor in metered amounts; after about one minute, a temperature of 43° C. prevailed. After termination of the feeding step, the temperature dropped. The reactor had not been equipped with a cooling unit.

After about five minutes, the warm suspension of 34° C. was rapidly discharged onto a suction filter, and the filter cake was dried under vacuum. The weight of the dry product was 7.2 g, corresponding to a yield of about 97%. Purity above 99.6%.

EXAMPLE 3 (COMPARATIVE EXAMPLE)

In an agitator-equipped reactor, a so-called clear solution with a formaldehyde excess of about 12% is provided, and sodium methylate is fed in dosed amounts over 6–8 hours at 20° C. and with an excess of about 14%. The temperature in the reactor was maintained at 20° C. by cooling units. After another 2–4 hours of post reaction, the mixture is suction-filtered and washed three times with methanol.

The yield of 2-sodium-2-nitro-1,3-propanediol herein is, on the average, 95%. Purity is below 99%.

EXAMPLE 4 (COMPARATIVE EXAMPLE)

2-Sodium-2-Nitro-1,3-propanediol.2 $CH_3OH$ (Aci-Salt)

Quantities of Feed Material:
(1) 375 ml of methanol
(2) 45.8 g of nitromethane, 96% strength (=43.97 g 100% strength)=0.720 mol
(3) 51.0 g of paraformaldehyde=1.698 mol
(4) 0.3 ml of KOH, 33% strength; D 20°/4=1.319=0.007 mol
30% strength=0.85% mol
(6) 200 ml of methanol for washing Process:
A 1-liter agitated flask, equipped with thermometer and dropping funnel, was charged with (1), (2), (3) and (4) and heated for fifteen minutes to 65° C., during which step the initial suspension changed over into a clear solution upon reaching the boiling point of 65° C. Subsequently, the solution was cooled to 15° C. and (5) was added dropwise within forty minutes at a temperature of 15° C. At this temperature, the mixture was stirred for another 1½ hours, and the thus-formed solid matter was suctioned off via a porcelain suction filter, washed in portions with (6) and dried.

Yield: 144.9 g of colorless aci-salt=0.699 mol (97.08%). Purity: 98.5%.

EXAMPLE 5

Quantities of Feed Material:
(1) 188 ml of methanol
(2) 22.9 g of nitromethane, 96% strength=0.36 mol
(3) 23.05 g of paraformaldehyde=0.763 mol
(4) 0.2 ml of Na methylate solution, 30% strength=0.001 mol
(5) 68.10 g of Na methylate solution, 30% strength =0.38 mol
(6) 100.0 ml of methanol for washing Apparatus:
500 ml agitated flask, equipped with reflux condenser, thermometer and dropping funnel.

The process was performed as in Example 4, except that a temperature of 45° C. was maintained in the flask by condensed methanol flowing back out of the attached reflux condenser.

Within eight minutes, (5) was added. Additional agitating time was ten minutes. Yield: 97.8%.
Purity: 99.7%.

It will be appreciated from the above examples that the process of this invention provides high yields of very pure salt product, i.e., the sodium salt of 2-nitro-1,3-propanediol in a few minutes.

In all foregoing examples, the yield refers to the so-called aci-salt, i.e. the methanol adduct of the sodium salt of 2-nitro-1,3-propane diol.

The Na methylate solution used has contents of 20 to 35 wt. % in methanol.

The preferred pressure is 50 to 600 mb.

What is claimed:

1. A process for the production of the sodium salt of 2-nitro-1,3-propanediol by reacting methanolic reaction solutions of nitromethane with paraformaldehyde containing alkali hydroxide by means of further reaction with sodium methylate in a methanolic solution, characterized in that the reaction solution and/or a residual solution from the production of the sodium salt of 2-nitro-1,3-propanediol is conveyed along one route, and sodium methylate in a methanolic solution is conveyed along another route to a reactor, and in that reaction temperatures are maintained at between 35° C. and at most 50° C. by evaporative cooling of vaporizing methanol by regulating the pressure in the reactor, which pressure is maintained below normal pressure.

2. A process according to claim 1, characterized in that the reaction temperature is maintained between 42° C. and 45° C.

3. A process according to claim 1, characterized in that an excess of paraformaldehyde amounts to 3–10 mol-% in the solution.

4. A process according to claim 2, characterized in that an excess of paraformaldehyde amounts to 3–10 mol-% in the solution.

5. A process according to claim 3, characterized in that an excess of sodium methylate amounts to 3–10 mol-% in the solution.

6. A process according to claim 4, characterized in that an excess of sodium methylate amounts to 3–10 mol-% in the solution.

7. A process according to claim 1, characterized in that the reactor is equipped with an agitator and a reflux condensor for receiving the vaporizing methanol that effects the evaporative cooling of contents of the reactor.

8. A process according to claim 1, characterized in that the pressure in the reactor is regulated to ensure that vaporation of methanol takes place in the reactor at the respective reaction temperature and the time of reaction within the reactor is about 10 to 25 minutes.

9. A process according to claim 1, characterized in that the pressure in the reactor is maintained at 50 to 5,000 mb.

* * * * *